United States Patent
Pizaine et al.

(10) Patent No.: US 10,413,258 B2
(45) Date of Patent: Sep. 17, 2019

(54) MEDICAL PLACEMENT ALARM

(71) Applicant: KONINKLIJKE PHILIPS N.V., Eindhoven (NL)

(72) Inventors: Guillaume Julien Joseph Pizaine, Issy-les-Moulineaux (FR); Olivier Pierre Nempont, Suresnes (FR); Vincent Maurice André Auvray, Meudon (FR); Raoul Florent, Ville D'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 23 days.

(21) Appl. No.: 15/747,330

(22) PCT Filed: Jul. 26, 2016

(86) PCT No.: PCT/EP2016/067828
§ 371 (c)(1),
(2) Date: Jan. 24, 2018

(87) PCT Pub. No.: WO2017/017110
PCT Pub. Date: Feb. 2, 2017

(65) Prior Publication Data
US 2018/0214095 A1 Aug. 2, 2018

(30) Foreign Application Priority Data
Jul. 27, 2015 (EP) ..................................... 15306218

(51) Int. Cl.
*A61B 6/12* (2006.01)
*A61B 6/00* (2006.01)
(Continued)

(52) U.S. Cl.
CPC ................ *A61B 6/12* (2013.01); *A61B 6/481* (2013.01); *A61B 6/487* (2013.01); *G06T 7/215* (2017.01);
(Continued)

(58) Field of Classification Search
None
See application file for complete search history.

(56) References Cited

U.S. PATENT DOCUMENTS

| 5,411,552 A * | 5/1995 | Andersen | A61F 2/2418 137/343 |
| 2007/0208250 A1* | 9/2007 | Sullivan | A61B 5/064 600/410 |

(Continued)

OTHER PUBLICATIONS

Karar et al. "Aortic Valve Prosthesis Tracking for Transapical Aortic Valve Implantation." International Journal of Computer Assisted Radiology and Surgery. (2011) 6:583-590.*

(Continued)

*Primary Examiner* — Luther Behringer

(57) ABSTRACT

An apparatus for generating a medical device implantation warning includes a processor to automatically generate a spatial implantation envelope of a first medical device. The envelope defines a spatial extent of a region of implantation around a first medical device prior to, during, and/or after deployment of the first medical device for implantation. If a second medical device, such as a pigtail catheter, strays into the area, an alarm is generated to warn a medical professional to withdraw the pigtail catheter, before deployment continues.

12 Claims, 7 Drawing Sheets

(51) Int. Cl.
*G06T 7/215* (2017.01)
*A61B 6/10* (2006.01)
*A61B 34/20* (2016.01)
*A61B 90/00* (2016.01)

(52) U.S. Cl.
CPC .............. *A61B 6/102* (2013.01); *A61B 90/39* (2016.02); *A61B 2034/2065* (2016.02); *A61B 2090/376* (2016.02); *G06T 2207/10121* (2013.01); *G06T 2207/30101* (2013.01)

(56) References Cited

U.S. PATENT DOCUMENTS

| | | | |
|---|---|---|---|
| 2008/0140010 A1 | 6/2008 | Kennedy | |
| 2010/0010488 A1* | 1/2010 | Kassab | A61B 18/1492 606/41 |
| 2011/0282189 A1 | 11/2011 | Graumann | |
| 2012/0177277 A1* | 7/2012 | Florent | A61B 5/02007 382/132 |
| 2013/0025934 A1 | 1/2013 | Aimi | |
| 2013/0072786 A1 | 3/2013 | Keogh | |
| 2014/0294152 A1 | 10/2014 | Florent | |
| 2014/0296970 A1 | 10/2014 | Ekvall | |

OTHER PUBLICATIONS

Karar, M.E. et al "A Simple and Accurate Method for Computer-Aided Transapical Aortic Valve Replacement", Computerized Medical Imaging and Graphics, 2014.

Edwards Lifesciences LLC. (Apr. 2011). Edwards SAPIEN—Transcatheter Heart Valve with the RetroFlex 3 Delivery System—Instructions for Use. FDA.

Medtronic, I. (2014). Medtronic CoreValve System—Transcatheter Aortic Valve Delivery Catheter System—Instructions for Use. FDA.

Cheung, Anson et al "Illustrated Techmiques for Transapical Aortic Valve Implantation", Ann Cardiothorac Surgery, vol. 1, No. 2, 2012, pp. 231-239.

* cited by examiner

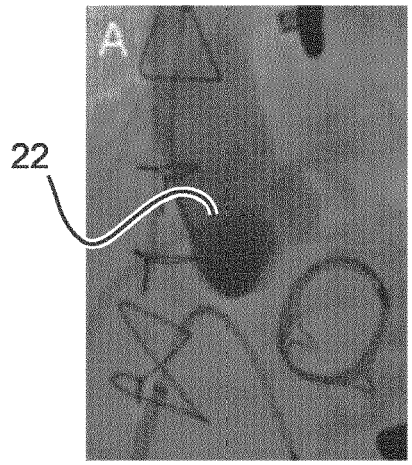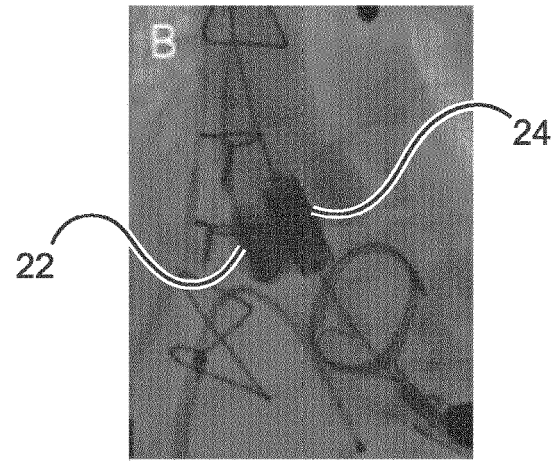
Fig. 2a  Fig. 2b
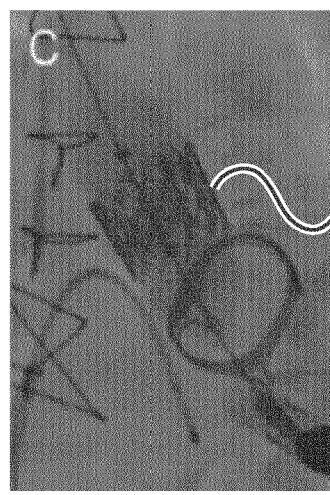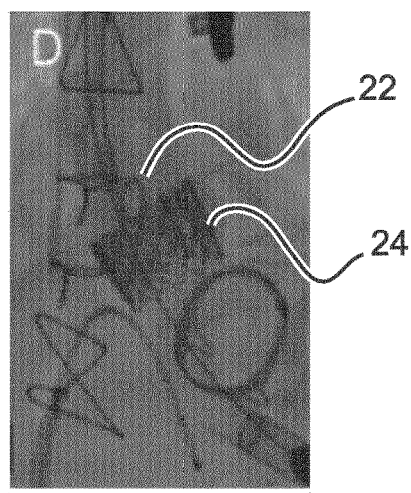
Fig. 2c  Fig. 2d

MEDICAL PLACEMENT ALARM

CROSS-REFERENCE TO PRIOR APPLICATIONS

This application is the U.S. National Phase application under 35 U.S.C. § 371 of International Application No. PCT/EP2016/067828, filed on Jul. 26, 2016, which claims the benefit of European Patent Application No. 15306218.7, filed on Jul. 27, 2015. These applications are hereby incorporated by reference herein.

FIELD OF THE INVENTION

The present invention relates to an apparatus for providing a medical placement alarm, a method for providing a medical placement alarm, an X-ray imaging arrangement, a computer program element, and a computer-readable medium.

BACKGROUND OF THE INVENTION

A medical device implantation procedure is used when it is necessary to implant a medical device inside a patient. Typically, a guide wire or intervention device, supporting a medical device to be implanted, is arranged in a lumen of a patient. A catheter can be used to emit bursts of contrast medium, detectable using a suitable fluoroscopic approach, to better visualize the anatomy. During such an intervention, an implant is deployed very quickly. The point of implantation or deployment of the medical device is a critical time period. Many actions need to be performed by a medical professional, in quick succession. Mistakes made in this procedure can lead to malpositioning or disruption of the medical device following the implantation. This increases the risk of future device failures or complications.

An article by Karar M. E. et al., "A simple and accurate method for computer-aided transapical aortic valve replacement", Comput Med Imaging Graph (2014), describes the fusing of a 3D aortic mesh model and anatomical valve landmarks with live 2D fluoroscopic images. Using the aortic mesh models, a target area for valve implantation is automatically estimated. The mesh model, landmarks and target area can be overlaid onto the fluoroscopic images by approximating the aortic root motion from the motion of a pigtail catheter without contrast agent.

US 2013/0259341 concerns image fusion during a TAVI (Transcatheter aortic valve implantation) procedure. However, feedback provided to a medical professional during an implantation procedure could be further improved.

SUMMARY OF THE INVENTION

It would be advantageous to have an improved technique for use during the implantation of a medical device.

The object of the present invention is solved by the subject-matter of the independent claims, wherein further embodiments are incorporated in the dependent claims.

Towards this end, a first aspect of the invention provides a method for providing a medical placement alarm.

A method for generating a medical device implantation warning, comprising the steps of:
a) providing an X-ray image sequence comprising a plurality of X-ray frames of a region of interest of an object;
b) generating a spatial implantation envelope of a first medical device to be deployed in a region of implantation, wherein the spatial implantation envelope defines a spatial extent of the region of implantation during and/or after a deployment of the first medical device,
c) detecting, in the first X-ray frame, image data representing a second medical device located at a second medical device position inside the region of interest;
d) detecting a potential intersection condition of the spatial implantation envelope and the second medical device position;
e) generating the device implantation warning if the potential intersection condition between the spatial implantation envelope and the second medical device position is detected in step d).

According to a second aspect of the invention, an apparatus is provided for providing a medical placement alarm. The medical placement alarm comprises:
a processing unit.

The processing unit is configured to: provide an X-ray image sequence comprising a plurality of X-ray frames of a region of interest of an object, to identify, in a first X-ray frame of the plurality of X-ray frames, a region of implantation of a first medical device, to detect, in the first X-ray frame, image data representing a second medical device located at a second medical device position inside the region of interest, to detect a potential intersection condition of (i) the region of implantation of the first medical device, and (ii) the second medical device position, and to generate a device implantation warning if the intersection condition between the region of implantation of the first medical device and the second medical device position is detected.

According to a third aspect of the invention, there is provided: an X-ray imaging arrangement. The X-ray imaging arrangement comprises:
an X-ray image acquisition device with an X-ray source and an X-ray detector (96); and
an apparatus for providing a medical placement alarm as described previously.

The X-ray image acquisition device is configured to acquire image data of a region of interest of a patient, and to provide the image data to an interface of the apparatus for medical device implantation assistance.

According to a fourth aspect of the invention, there is provided a computer program element for controlling an apparatus according to the previous description, which, when the computer program element is executed by a processing unit, is adapted to perform the steps according to the previous description.

According to a fifth aspect of the invention, there is provided a computer-readable medium having stored the computer program element previously discussed.

An apparatus, method, X-ray imaging arrangement, computer program element, or computer-readable medium according to the above-discussed aspects have the effect that the position of a second medical device (for example, a pigtail catheter) may be assessed, and feedback provided, to reduce the risk that the second medical device could become snared or trapped under an implantable first medical device during implantation. It is possible to make this assessment before the actual step of implanting the first medical device in a region of implantation of a patient, or at the instant of implantation.

In this description, the term "region of interest of an object" means a portion of a patient's body of interest during an implantation procedure. For example, during a cardiac implantation, the region of interest would be the upper thorax of the patient. The term "region of implantation" means a region which is a subset of the region of interest of an object, and which is expected that a first medical device will be deployed. For example, in the case of a TAVI procedure, the region of interest is the cardiac area, and the region of implantation is the aortic root.

The term "spatial implantation envelope" means a region within the region of interest, in two-dimensional or three-dimensional space, which the first medical device will occupy at the start of an implantation procedure, during an implantation procedure, and by the end of the implantation procedure. In other words, every position occupied by the first medical device during its implantation or deployment defines the extent of the spatial implantation envelope. In one example, a spatial implantation envelope is a two-dimensional region comprising the undeployed first medical device, and having a shape boundary representing the extent of the fully deployed first medical device. In the case of a three-dimensional X-ray image, the spatial implantation envelope could be a three-dimensional volume.

The term "potential intersection condition" is a term defining a situation where another medical device enters the spatial implantation envelope of the first medical device. If a second medical device enters a spatial implantation envelope, there is a risk that when the first medical device is implanted, the first medical device will collide with, or trap, the second medical device. Therefore, the spatial implantation envelope could be considered to be a "danger zone" which another medical device should not enter shortly before an implantation of the first medical device, at the risk of causing a snare between the first and second medical devices.

In the following description, the term "first medical device implantation model" defines a geometrical, or mechanical model which describes the movement of a first medical device from an undeployed state to a deployed state. This information may be provided a priori, to enable the estimation of the space that a first medical device moves through during implantation. Additional data, such as from a CT roadmap, may be used to provide a boundary condition for the implantation model at a particular point in a patient. Therefore, it can be considered as an alternative view of the invention to define a "danger zone" around a first medical device, for example, shortly before an implantation of the first medical device. If another medical device strays within this danger zone shortly before and/or during implantation or deployment of the first device, an alarm further referred to as "device implantation warning" is triggered.

These, and other aspects, of the present invention will become apparent from, and be elucidated with reference to the embodiments described hereinafter.

BRIEF DESCRIPTION OF THE DRAWINGS

Exemplary embodiments of the invention will be described with reference to the following drawings:

FIG. 2a) to 2d) show X-ray images of a medical device implantation procedure similar to that shown schematically in FIG. 1.

DETAILED DESCRIPTION OF THE EMBODIMENTS

The placement of a medical device, for example a valve prosthesis during a TAVI procedure, is highly dependent on accurate positioning of the valve prosthesis on the supporting anatomy, for a successful outcome.

Classically, once a valve prosthesis has been placed in an implantation position, and the position of the valve has been confirmed using an angiogram, a classic valve deployment consists of the following steps:

Firstly, a heart pacemaker attached to the heart is put into a so-called "hyperpacing" mode to reduce the magnitude of the patient's heartbeat. Secondly, the valve prosthesis is deployed. In some types of valve, for example the Medtronic CoreValve™ the interventionist releases the proximal part of the prosthesis, confirms the position, pulls a pigtail catheter back, and then proceeds until the valve is fully deployed. In another type of valve deployment, for example the Edwards SAPIEN XT™ valve, the interventionist withdraws the pigtail catheter, and then inflates a balloon until the valve prosthesis is fully deployed. Thirdly, an additional angiogram is acquired to assess the final position of the valve.

A pigtail catheter is a catheter which is used for delivering contrast agent to a region of deployment of a valve prosthesis. To achieve successful positioning, the pigtail catheter should be positioned in an aortic cusp until the latest moment before deployment, in order to allow the clinician to visualize the aortic root by means of contrast injection until the latest moment. The pigtail catheter is withdrawn in the instant before implantation. This ensures that the pigtail catheter won't become entangled or trapped by the expanding frame of the valve prosthesis. After deployment, the pigtail catheter is often re-introduced, because contrast agent is often required to assess the outcome of the intervention.

Figure 1A:
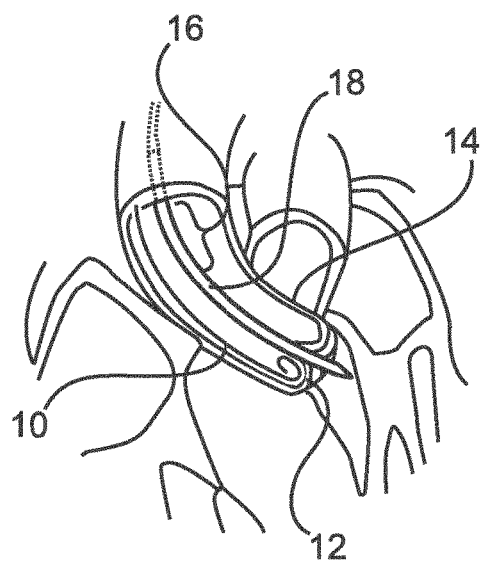
FIG. 1a) to FIG. 1c) show stages of the implantation of a medical device in an aortic valve, in schematic form.

FIG. 1a) to 1c) illustrate schematically the stages of a successful valve prosthesis placement. In FIG. 1a), the pigtail catheter 10 is shown within the aortic cusp 12 of the aorta 14. An undeployed valve prosthesis 16 is shown advancing, supported on a deployment device 18. The location of the pigtail catheter 10 in the aortic cusp enables contrast medium to be released close to structures important for a secure placement of the valve prosthesis on the aortic annulus, and thus helps with a successful placement of the valve.

Figure 1B:
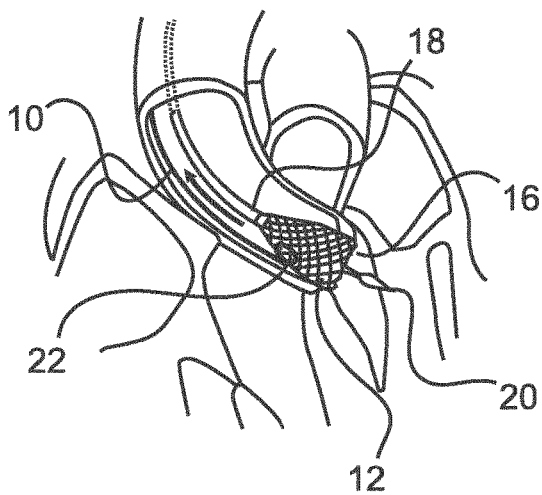
FIG. 1d) shows a medical device implantation failure mode.

FIG. 1b) shows that during deployment of the valve prosthesis, the deployment device 18 has advanced so that its distal tip 20 has penetrated through the aortic valve. The pigtail catheter 10 is still in the vicinity of the aortic cusp 12, and so comes very close to the expanding stent during expansion. The valve prosthesis 16 is shown partially deployed (the illustrated valve-prosthesis is an example of a self-expanding stent-valve). The pigtail catheter 10 has been withdrawn far enough so that it does not become trapped in an area 22 in the proximity of the self-expanding stent-valve.

Figure 1C:
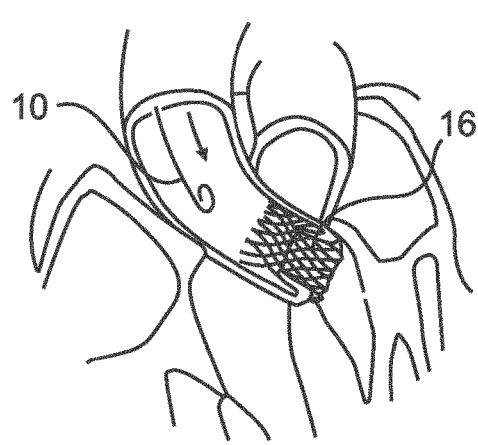
Figure 1D:
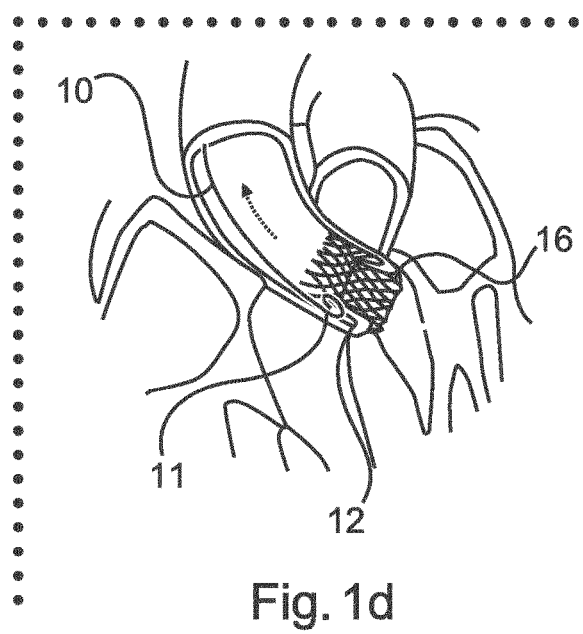

FIG. 1c) shows the deployed valve prosthesis 16. In this situation, the pigtail catheter 10 has been advanced back towards the valve prosthesis 16, to enable further contrast agent bursts to confirm the correct positioning of the valve prosthesis 16. FIG. 1d) illustrates a situation when the pigtail catheter 10 has not been withdrawn quickly enough. The valve prosthesis 16 is shown in a fully deployed state, but the pigtail catheter tip 11 is shown trapped underneath the expanded body of the valve prosthesis 16. The only way to remove the pigtail catheter 10 in this situation would be for the interventionist to tug hard on it. The shape of the distal end of the pigtail catheter 10 usually means that a snag between the valve prosthesis 16 and the tip 11 will occur, causing the valve to be dislodged partially, causing a paravalvular leak to result. The valve could even be completely dislodged from the aortic root.

Thus, a dilemma is that the longer the pigtail catheter remains in the aortic cusp, the longer the interventionist can inject contrast agent to visualize the aortic annulus, and to obtain a good placement. If the pigtail catheter is withdrawn too late, then it is trapped in the frame of the valve-prosthesis. Trying to retrieve the pigtail catheter forcefully may lead to complications.

Finding the optimal time to pull back the pigtail catheter is becoming more critical. New two-stage valve deployment techniques could allow the withdrawal of the catheter half-way through a deployment. In addition, some dynamic roadmapping approaches for TAVI procedures rely on tracking the position of the pigtail catheter in X-ray sequences, to improve the registration between the dynamic roadmap, and the X-ray image.

Therefore, it could be beneficial if the pigtail catheter stays in the aortic root as long as possible during deployment, to enable dynamic motion compensation, when such techniques are applied. Therefore, a technique is needed which enables an interventionist to know when a particular placement of a pigtail catheter could lead to that pigtail catheter becoming trapped during a deployment.

FIG. 2*a*) to 2*d*) illustrate a successful TAVI deployment. In FIG. 2*a*), a pigtail catheter 22 is shown releasing a cloud of contrast agent. In FIG. 2*b*), a baseline aortography is performed as a compressed valve prosthesis 24 is positioned in an aortic annulus, and contrast agent is released from the pigtail catheter 22 to confirm that the placement is correct. FIG. 2*c*) shows that the valve prosthesis 24 has expanded, but the pigtail catheter 22 has been withdrawn a sufficient distance so that it is not trapped. FIG. 2*d*) shows the positioned valve prosthesis 24, and the reinserted pigtail catheter 22, which is present to perform a final aortography.

Figure 3:
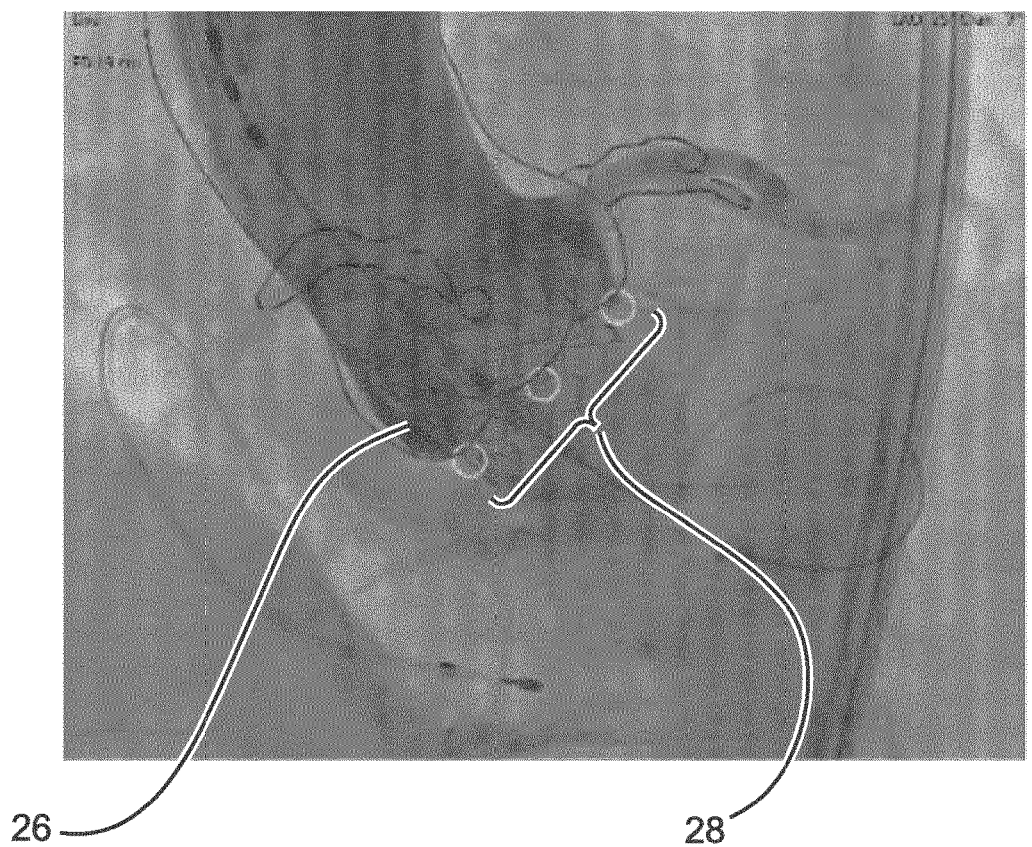
FIG. 3 shows an enhanced X-ray image of a problematic valve prosthesis deployment.

FIG. 3 shows a practical illustration of a pigtail catheter 26 which is trapped by the frame of a valve prosthesis 28. The pigtail catheter 26 is seen trapped between the outside of the frame of the expanded valve prosthesis 28, and the wall of the aortic valve. According to a first aspect of the invention, a method for providing a medical device implantation warning is provided, comprising the steps of:

a) providing (30) an X-ray image sequence comprising a plurality of X-ray frames of a region of interest of an object;
b) generating (32) a spatial implantation envelope of a first medical device to be deployed in a region of implantation, wherein the spatial implantation envelope defines a spatial extent of the region of implantation during and/or after a deployment of the first medical device;
c) detecting (34), in the first X-ray frame, image data representing a second medical device located at a second medical device position inside the region of interest;
d) detecting (38) a potential intersection condition of the spatial implantation envelope and the second medical device position;
e) generating (40) a device implantation warning if the potential intersection condition is detected in step d).

According to the first aspect, it is possible to warn a user that a second medical device is positioned inside a spatial implantation envelope, giving rise to a situation where an intersection between the second medical device and the first medical device, if the first medical device was to be deployed at that instant.

Figure 4:
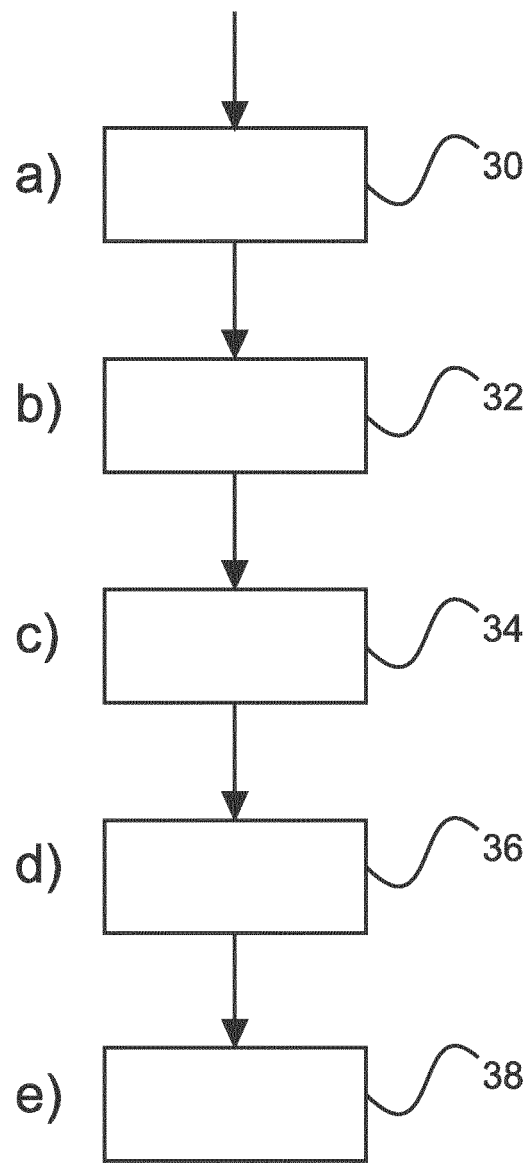
FIG. 4 shows a method according to the first aspect.

FIG. 4 illustrates the method according to the first aspect.

In step a), an X-ray image sequence is provided from, for example, a X-ray apparatus. In a TAVI procedure, the X-ray apparatus would be positioned over the cardiac region of a patient, at an angle which provides an effective view of an aortic annulus of a patient.

In step b), an identification of a region of implantation of a first medical device can occur without the first medical device being present in the region of interest. For example, in an embodiment, the position of the region of implantation and/or the spatial implementation envelope of the first medical device is deduced from the recognition of an anatomical feature in one or more X-ray image frames of the sequence. As an example, the aortic annulus is an example of a reasonably distinct anatomical feature used to anchor a valve prosthesis. Identification of the aortic annulus could, thus, provide a good estimate of the region of implantation and the spatial implantation envelope. For the latter, preferably, information regarding the device to be deployed, such as an implantation model, should be available. In some subsequent embodiments, the first medical device is explicitly detected in the region of interest.

Optionally, the region of implantation and/or the spatial implantation envelope may be defined by a medical professional using coordinates, input into an input interface provided with the apparatus, such as a graphical user interface. Alternatively, the coordinates are provided from a system connected to the apparatus.

The first state of the first medical device can be considered to be an undeployed state, or an unimplanted state. The second state of the first medical device can be considered to be an implanted state, or a deployed state of the first medical device.

In step c), the detection 34 of image data representing a second medical device located at a second medical device position may be performed using image processing techniques applied to the first X-ray frame known to the person skilled in the art. For example, in the case that the second medical device is a pigtail catheter, an image processing algorithm can be provided which detects the presence of a region of image data having a long, thin form, with a curled distal end. The image processing algorithm would label this image data as being indicative of a second medical device position. Alternatively, the image processing algorithm could track the source of contrast bursts, to find the distal end of the pigtail catheter.

In step d), the detection of a potential intersection condition of the region of implantation and the second medical device position comprises the identification of at least one pixel within the region of implantation which is also shared with a pixel of the detected image data representing the second medical device.

Optionally, the shape of the region of implantation is defined as a simple shape (such as a square, rectangle, circle, oval, ellipse, etc). The simple shape is positioned at a position of the region of implantation identified in step b) above.

Optionally, the shape of the region of implantation is defined using the position of the region of implantation identified in step b) above. The outer extent of the region of implantation is defined with reference to an anatomical boundary defined by a 3D roadmap, or a 2D roadmap of the patient. Alternatively, the outer extent of the region of implantation may be defined by reference to 3D CT or MRI data, or anatomical information derived from the X-ray image sequence.

Optionally, an internal threshold between the second medical device position and a boundary of the region of implantation may be defined. In other words, the device implantation warning would be generated only if the second medical device was found to extend a certain threshold inside the region of implantation. This measure would provide a threshold to ensure that the alarm was not generated repetitively in conditions when the catheter was very close to the region of implantation.

Optionally, an external threshold between the second medical device position and a boundary of the spatial implantation envelope may be defined. A device implantation warning may be generated if the second medical device position is within the threshold. Therefore, an additional safety buffer may be provided during the withdrawal of a second medical device during a device implantation.

In step e), a device implantation warning is generated if a potential intersection condition between the region of implantation and the second medical device position is detected. Optionally, the warning is an audible alarm.

Optionally, the warning is provided as visual feedback on the screen of a X-ray apparatus. For example, the border of the screen of a X-ray apparatus could flash red. Alternatively, markers, or flashing lights could be provided around the trace of the first medical device, or the second medical device, or the distal tip of the second medical device in the fluoroscopy screen.

Optionally, the shape, or outline of the region of implantation is superimposed onto a fluoroscopy system screen to enable an interventionist to identify the spatial implantation envelope at all times during the procedure.

According to the above-described method, a method is provided for providing a medical device alarm for an instance when a second medical device is in a region of implantation of a first medical device.

According to an embodiment, the method described above further comprises the steps of:

c1) detecting, in the first X-ray image frame, image data representing the first medical device, having a first medical device position; and c2) generating a spatial implantation envelope of the first medical device at the first medical device position, wherein the spatial implantation envelope defines the spatial extent of the region of implantation during, and/or after a transition of the first medical device between a first and a second state.

In step c1), image detection techniques, such as segmentation and/or image recognition are used to identify a first medical device, and its position.

In step c2), the generation of the spatial implantation envelope of the first medical device can be performed according to pre-provided data. In other words, if a specific type of valve is being implanted, the spatial implantation envelope details would be uploaded into an apparatus, or programmed manually.

In a 2D X-ray image, for example, the spatial implantation envelope could be represented as a two-dimensional region (polygon) containing the first medical device, and the extent of the two-dimensional region will represent the furthest extent of the first medical device when implanted. It follows that if a pigtail catheter is present in the spatial implantation envelope, there is an implied risk that during expansion or implantation of the first medical device, the pigtail catheter will become trapped between the expanding first medical device and the lumen into which the first medical device is being deployed.

According to an embodiment, the spatial implantation envelope could be a simple shape sized to fit the first implantation device. Alternatively, the spatial implantation envelope could be a complex shape tracking the shape of the first implantation device.

According to an embodiment, the spatial implantation envelope represents the extent of the region of interest occupied during an implantation from a first state to a second state. For example, for an expandable stent valve, the spatial implantation envelope will represent the maximum extent after expansion of the stent valve from a compressed first state to an expanded second state Optionally, the region of implantation of the first medical device can be identified by detecting the first medical device in the X-ray image, in its first state, before an implantation.

Optionally, the spatial implantation envelope is a three-dimensional volume, or a two dimensional region.

FIG. 5 illustrates an exemplary medical device implantation scenario. In FIG. 5, a TAVI (transcatheter aortic valve implantation) procedure is shown. In FIG. 5, a first medical device 46 can be seen, which is a valve mounted on a self-expanding stent which expands when a sheath is withdrawn. The spatial implantation envelope 50 will, at its top and bottom extent, be defined by the lumen walls 40. The spatial implantation envelope is defined at its proximal and distal extent by the width of the first medical device 44.

It will be appreciated that in FIG. 5, the deployment territory (region of implantation/spatial implantation envelope 50) is determined with respect to the stent of the prosthesis. However, this is only characteristic to the type of valve shown in FIG. 5. It will be appreciated that a wide range of valves may have differently shaped deployment territories depending on their design. Other types of device may not have a sheath, or may be balloon-expandable, stentless, and could also be used with the technique addressed herein.

Figure 5A:
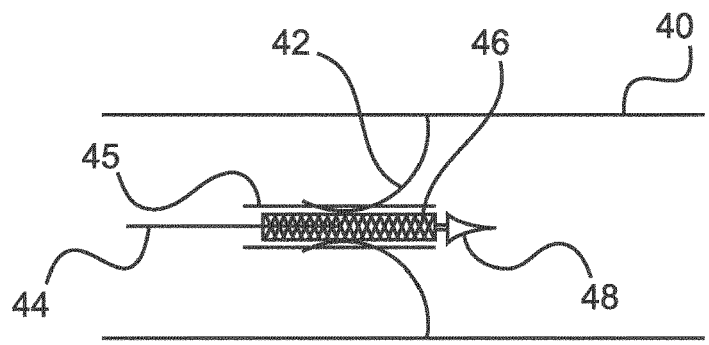
FIG. 5a) to 5d) show an example of spatial envelope generation during implantation, in schematic form.
Figure 5B:
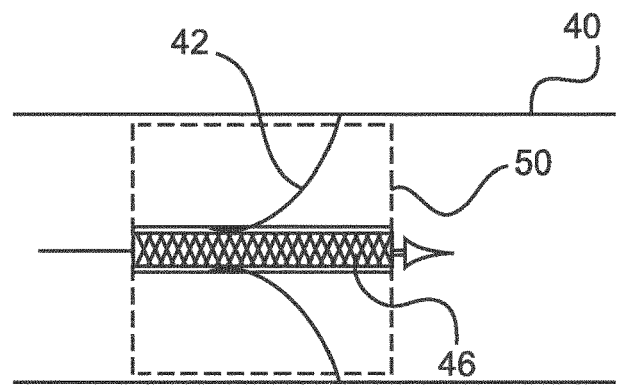
Figure 5C:
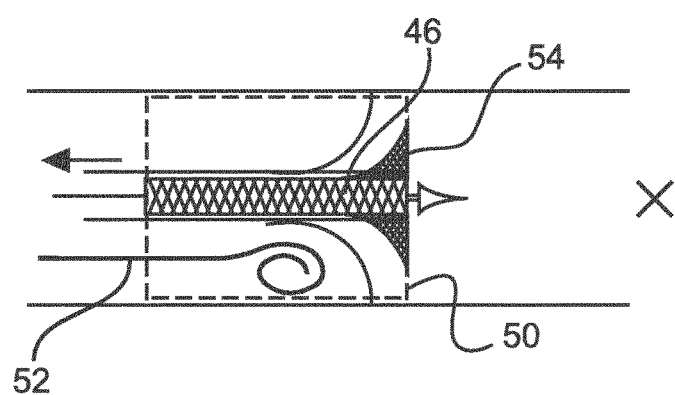
Figure 5D:
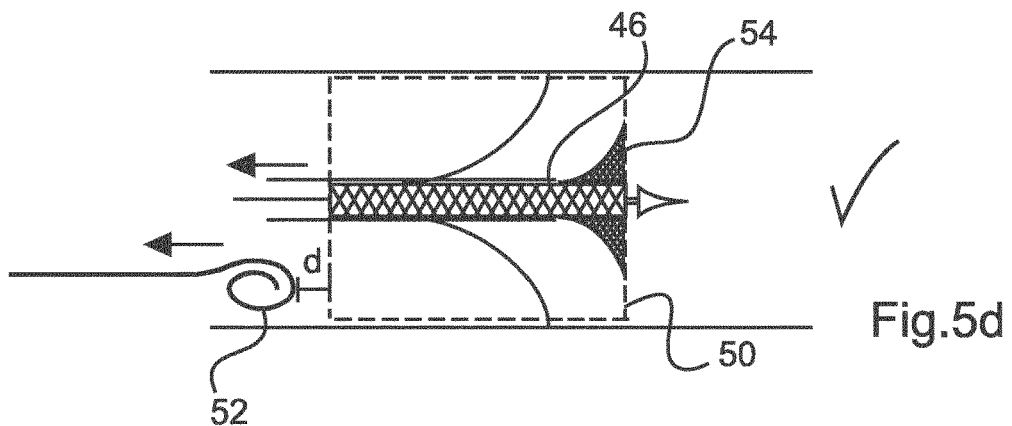

FIGS. 5a) to FIG. 5d) show a schematic view of the deployment of a first medical device in the presence of a second medical device when an example of the method described above is used.

FIG. 5a) shows a body lumen wall 40 such as an aorta. Features resembling an aortic valve are shown at 42. In FIG. 5a), an intervention device 44 comprising an undeployed valve prosthesis 46 constrained by a deployment sheath 45 is shown. At the distal end of the intervention device 44 is a guide wire tip 48.

FIG. 5b) shows a situation when a spatial implantation envelope of the first medical device is generated. The spatial implantation envelope 50 is shown at a dotted line rectangle around the extent of the first medical device 46.

The implantation envelope may be generated according to the current position of the intervention device 44, as shown here. Alternatively, the implantation envelope position may be generated based on an image recognition of an anatomical feature, such as the aortic valve 42. Alternatively, the implantation envelope position is pre-programmed by an interventionist; for example, the spatial implantation envelope may be input into the apparatus by means of a suitably configured graphical user interface.

FIG. 5c) shows a situation where the second medical device, in this example a pigtail catheter 52, is inserted within the region of the spatial implantation envelope 50. The spatial implantation envelope 50 coincides with the position of the second medical device 52, and it is determined that a potential intersection condition is present. In addition, the first medical device 46 is in a situation where it has begun to deploy, as seen by the expanding distal end 54. This is a dangerous situation, because if the valve prosthesis continues to deploy, the second medical device 52 (pigtail catheter) will be trapped by the expanded first medical device (valve-prosthesis).

FIG. 5*d*) also shows a situation where the first medical device 46 is in the process of implantation. The second medical device (pigtail catheter) 52 has been withdrawn in sufficient time. Therefore, the second medical device has left the spatial implantation envelope 50, and there is no risk of the second medical device 52 becoming trapped underneath the expanded first medical device 46. Therefore, in this case, a potential intersection condition is not present, and the device implantation warning is not generated.

The numeral d denotes a distance between the extent of the second medical device 52 and the extent of the spatial implantation envelope which, according to an embodiment, may function as a placement threshold, so the alarm may be triggered if the second medical device is outside the region of the spatial implantation envelope, but too close to the spatial implantation envelope for a safe deployment.

According to an embodiment, a method is provided as discussed previously, further comprising the step of:
a1) providing a first medical device implantation trigger; and
wherein the steps b), c), d), e) and f) are performed in the case that the first medical device implantation trigger signal indicates that a first medical device implantation is (i) imminent, or (ii) has begun.

According to this embodiment, a number of stimulus signals may be provided to ensure that the potential intersection condition can be identified imminently before a deployment of a first medical device.

According to an embodiment, the first medical device implantation trigger is the activation of a hyperpacing mode of a pacemaker used in the intervention. As the point of device deployment approaches, certain protocols utilize a hyperpacing mode. This involves the application of electrical signals to the heart to reduce, or to stop, the amplitude of the heart. Therefore, the engagement of a hyperpacing mode is an indication that can be used to define the time of a first medical device implantation trigger.

According to an embodiment, the first medical device implantation trigger is provided when a set of imaging system parameters are engaged. For example, a distinctive set of parameters of the imaging system will be used when the imaging system is focused on a specific region in the region of interest, to give a good view of the implantation of the first medical device. Therefore, a system could detect the engagement of a distinctive set of parameters of the imaging system (for example, zoom and/or angle), and provide a first medical device implantation trigger when the distinctive set of parameters were used. In other words, the imaging setup parameters could be used to infer the time of a first medical device implantation trigger.

According to an embodiment, the first medical device implantation trigger is provided based on a specific configuration of any one, or a combination, of settings selected from, but not limited to, the group of angulation of the imaging system, field of view of the imaging system, exposure mode, contrast injection status, and frame rate.

According to an embodiment, the first medical device implantation trigger is a balloon inflation signal. Many types of medical devices are implanted using a balloon. Therefore, a signal to inflate the balloon can be used as a first medical device implantation trigger.

According to an embodiment, the movement of a set of radiopaque valve markers is monitored, using image processing techniques. Self-expanding valve prostheses use radiopaque markers to inform a medical professional of the position of a stent sheath during withdrawal. When the radiopaque valve markers begin to move, the first medical device implantation trigger is provided.

According to an embodiment, the first medical device implantation trigger is provided, based on the expansion of the first medical device. The first medical device is monitored, and if its distal, or proximal end, begin to expand, an indication is present that a stent-valve sheath is being withdrawn. An image processing algorithm may be used to monitor changes in the shape of the valve indicating an expansion of the first medical device.

According to an embodiment, the input signals are monitored and analyzed on a regular basis. In the case of control signals for balloon inflation or a pacemaker control signal, the control signals are monitored every few milliseconds. If the first medical device implantation trigger is derived from the X-ray images in the X-ray frames, every frame, or a certain number of frames may be monitored to detect the first medical device implantation trigger.

According to an embodiment of the invention, the first medical device implantation trigger is generated from an ensemble of input signals.

For example, a more accurate determination of the beginning of an implantation of a first medical device can be derived, if an ensemble of signals is used.

In a specific example, the ensemble comprises (i) the detection of the engagement of the hyperpacing mode, and (ii) the detection of the expansion of the first medical device during the implantation. This is advantageous because the engagement of the hyperpacing mode indicates an imminent intention to implant the first medical device, but the detection of the actual expansion of the first medical device could be used to indicate the application of a threshold to ensure that the spatial implantation envelope is a specified distance away from the second medical device by the time the first medical device has been implanted along its full extent.

Figure 6:
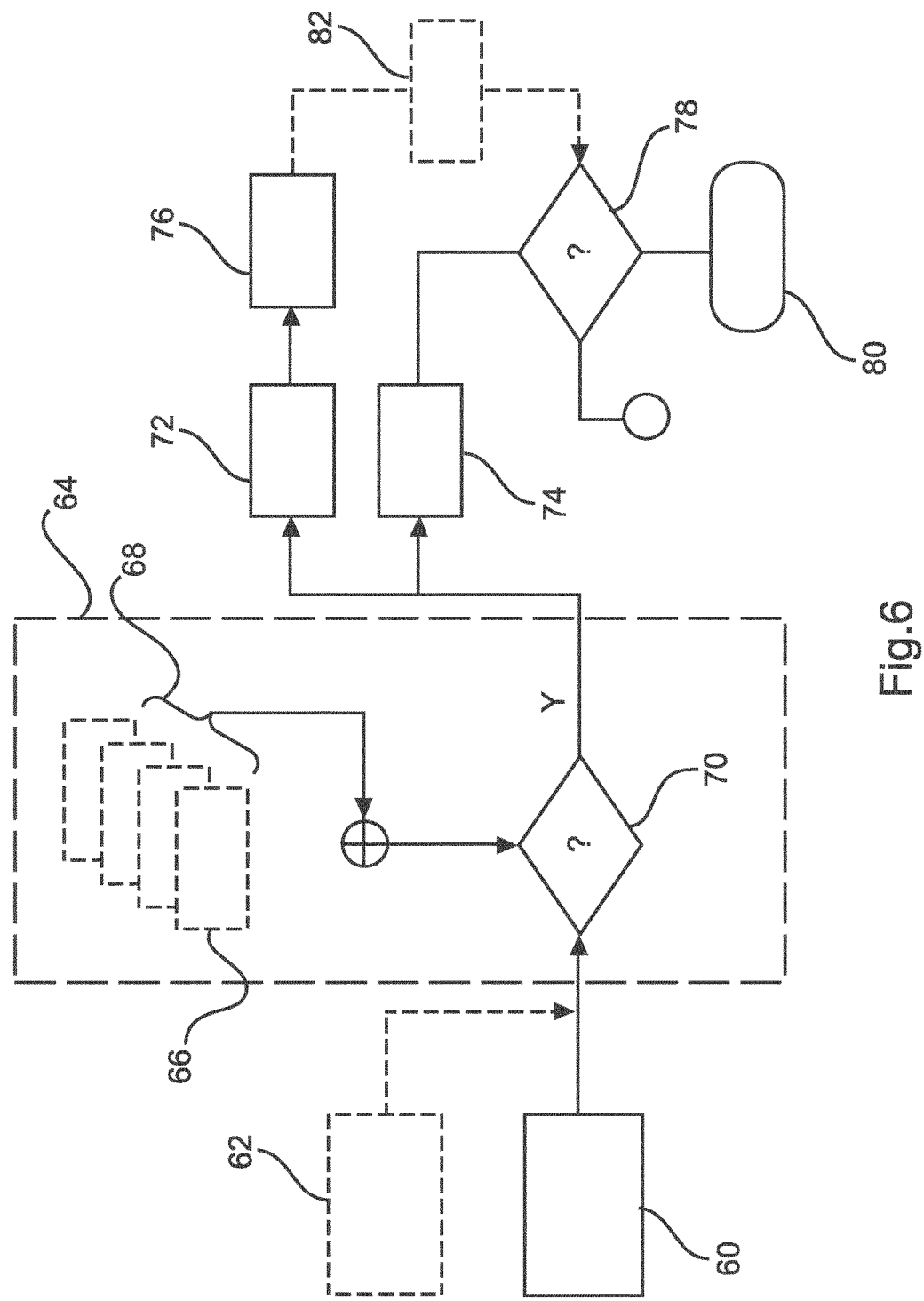
FIG. 6 shows a block diagram of an example implementation.

FIG. 6 shows a specific implementation of the embodiment of the method discussed above.

In the embodiment of FIG. 6, a medical device implantation detection unit 64 checks for the occurrence of one event 66, or a plurality of events 68, indicating an implantation trigger. As discussed above, a combination of conditions defining a first medical device implantation can be defined.

Decision box 70 represents the detection of a medical device implantation. If a medical device implantation condition is detected, a detection in an X-ray image of a first medical device, such as a valve prosthesis, occurs at 72. The detection in an X-ray image of a second medical device, for example a pigtail catheter, occurs at box 74.

The spatial implantation envelope for the first medical device is computed at 76. A decision is taken at box 78 as to whether, or not, the second medical device will be within the region of implantation of the first medical device. In other words, the detection of a potential intersection condition is made at decision point 78. A device implantation warning 80 is generated if the potential intersection condition is found to be true. Box 82 is an optional feature illustrating the fact that the medical device implantation monitoring may occur continuously.

According to an embodiment of the invention, there is provided a method as described previously, further comprising the step of:

g) outputting the device implantation warning.

As discussed previously, the device implantation warning may take the form of an audible alarm, an illumination on a X-ray screen of a potential intersection condition, or a coloured flashing border around the screen. In other words, the device implantation warning alerts a medical professional about the risk of a potential intersection condition occurring between a first medical device and a second medical device.

According to an embodiment, there is provided a method according to any preceding claim, further comprising the steps of:

b1) providing a first medical device implantation model of the first medical device; and d1) simulating an implantation phase between a first simulated implantation state and a second simulated implantation state of the first medical device inside the region of interest using the first medical device implantation model; and d2) providing the spatial implantation envelope using the second simulated implantation state.

According to this embodiment, a geometrical or dynamic model of a first medical device during implantation is provided. By simulating the expansion of the first medical device using the first medical device implantation model, a more accurate spatial implantation envelope can be provided, resulting in a more accurate estimate of a potential intersection condition of the first medical device and the second medical device.

According to an embodiment of the invention, there is provided a method according to the previous description of step b1), step d1), and step d2). The method comprises the steps of:

a2) receiving a partial implantation indication; and wherein in step d1), the first medical device implantation model represents a partially implantable first medical device; and wherein in step d), the spatial implantation envelope of the first medical device represents an intermediate implantation position of the first medical device inside the region of interest; and wherein step f) further comprises:

f1) generating an intermediate device implantation warning upon receiving the partial implantation indication, if the intermediate implantation position intersects with the second medical device position.

According to this embodiment, a supplementary signal indicating deployment of the first implantation device is provided as a partial implantation indication. Modern valve prostheses often have a two-phase implantation, where a partial expansion is made to enable initial positioning on an aortic annulus, and then a full implantation of the prosthesis is provided if the partial positioning is correct.

Therefore, a partial implantation indication can be provided, for example, using image recognition algorithm to recognize a partial implantation state of a first medical device. The spatial implantation envelope will differ for the two-stage implantable first medical device. A second medical device may be acceptably positioned when the partial deployable first medical device is in a partially deployed position, but the second medical device may be in an unacceptable position if the first medical device proceeds to full deployment. Therefore, this embodiment generates an intermediate device implantation warning if an intermediate implantation position of a first medical device intersects with the second medical device position.

According to an embodiment of the invention, a method is provided as discussed previously, further comprising the steps of:

a3) providing an anatomical roadmap of the region of interest of the object;

c3) registering the first X-ray frame to the anatomical roadmap to yield the registered X-ray frame;

c4) obtaining a constraint condition of the region of implantation using the anatomical roadmap; and wherein in step d), the spatial implantation envelope of the first medical device is generated using the constraint condition.

Anatomical roadmaps, in three-dimensional or two-dimensional form, can be provided following, for example, a CT examination of the patient. The anatomical roadmap of a section, for example, of an aorta in the region of interest of the object provides a constraint to the implantation of a first medical device. Therefore, a segment of an anatomical roadmap in a region of interest, and more specifically a region of implantation of a first medical device forms a constraint condition which may be used as a spatial implantation envelope.

Therefore, according to this embodiment, a more accurate outer extent of the spatial implantation envelope may be defined.

According to an embodiment, a method is provided as discussed previously, wherein the first medical device is a deployable valve prosthesis (of either the self-expanding stent, or balloon-expandable type). The second medical device is a pigtail catheter.

According to this embodiment, the potential intersection condition may be detected during a TAVI procedure involving the positioning of a valve prosthesis in an aortic annulus.

Another medical procedure involving an intervention into the heart is "left atrial appendage and closure". The left atrial appendage is a small sac present in some patients, in the wall of the left atrium. When the heart is in a fibrillating state, blood can collect in the left atrial appendage and clot. One option for treating a left atrial appendage is to fit it with a device to close it. Therefore, it also involves an intra-cardiac intervention and the use of contrast medium delivered via a pigtail catheter.

According to an embodiment of the invention, a method is provided as discussed previously, wherein the first medical device is a left atrial appendage occlusion device, and the second medical device is an electrode for use in a left atrial appendage procedure.

In a left atrial appendage procedure, an electrode may be used in the vicinity of an occlusion device, and it is important that the electrode does not become snared in the occlusion device as the occlusion device changes the shape.

According to an embodiment, a method is provided as discussed previously, further comprising the step a4):

a4) detecting the first medical device in the first X-ray frame of the plurality of X-ray frames.

It is not a requirement of the method according to the first aspect that the first medical device is detected within the X-ray image sequence. This is because it is possible to define the position of the first medical device using an external input, or using a cursor on a screen of a fluoroscopy system. However, according to this embodiment, the first medical device may be detected in the first X-ray frame. Therefore, the position of the spatial implantation envelope would be defined according to the motion of the first medical device on a delivery system, for example on a guide wire.

According to a second aspect of the invention, an apparatus 82 for providing a medical placement alarm. The apparatus comprises:

a processing unit 84;

wherein the processing unit is configured to: provide an X-ray image sequence comprising a plurality of X-ray frames of a region of interest of an object, to identify, in a first X-ray frame of the plurality of X-ray frames, a region of implantation of a first medical device, to detect, in the first X-ray frame, image data representing a second medical device located at a second medical device position inside the region of interest, to detect a potential intersection condition of (i) the region of implantation of the first medical device, and (ii) the second medical device position, and to generate a device implantation warning if the potential intersection condition between the region of implantation of the first medical device and the second medical device position is detected.

Figure 7:
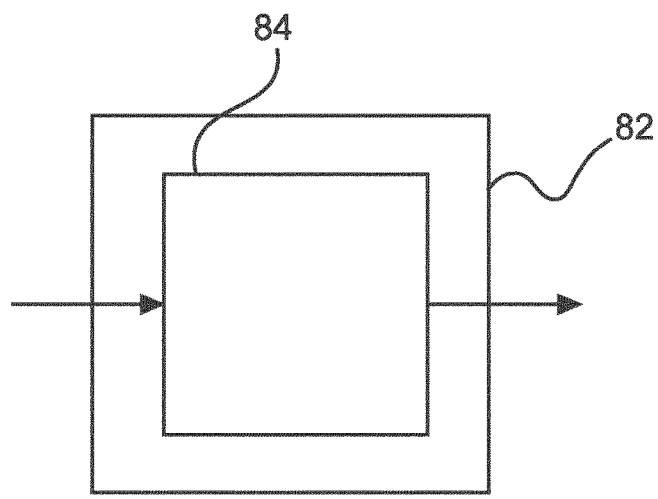
FIG. 7 shows an apparatus for providing a medical placement alarm according to a second aspect of the invention.

FIG. 7 shows an apparatus 82 for providing a medical placement alarm.

According to this second aspect of the invention, an apparatus 82 is provided which enables a warning to be provided to a medical professional if a second medical device is at risk of becoming and snared on a first medical device during implantation.

According to an embodiment, the processor 84 is further configured to: detect, in the first X-ray image frame, image data representing the first medical device, having a first medical device position.

The processor is further configured to: generate a spatial implantation envelope of the first medical device at the first medical device position, The spatial implantation envelope defines the region of implantation during, and/or after a transition of the first medical device between a first and a second state. According to an embodiment, an apparatus 82 as described previously is provided. The apparatus further comprises:

an input unit.

The input unit is further configured to provide a first medical device implantation trigger to the processing unit 84.

The processing unit 84 is configured to generate a device implantation warning if a potential intersection condition between the spatial implantation envelope and the second medical device position is detected, if the first medical device implantation trigger signal indicates that a first medical device implantation is (i) imminent, or (ii) has begun.

According to an embodiment, an apparatus 82 is provided as previously described, wherein the apparatus further comprises:

an output unit, wherein the output unit is configured to output the device implantation warning.

According to an embodiment, an apparatus 82 is provided, as described previously, wherein the processing unit 84 is further configured to provide a first medical device implantation model of the first medical device, to simulate an implantation phase between a first simulated implantation state and a second simulated implantation state of the first medical device inside the region of interest using the first medical device implantation model, and to provide the spatial implantation envelope using the second simulated implantation state.

According to an embodiment, an apparatus 82 is provided according to the previous description, wherein the processing unit 84 is further configured to receive a partial implantation indication. The first medical device implantation model represents a partially deployable first medical device; and the spatial implantation envelope of the first medical device represents an intermediate implantation position of the first medical device inside the region of interest.

The processing unit 84 is configured to generate an intermediate device implantation warning upon receiving the partial implantation indication, if the intermediate implantation position intersects with the second medical device position.

According to an embodiment, the apparatus 82 is provided as described previously, wherein the processing unit 84 is further configured to provide an anatomical roadmap of the region of interest of the object, to register the first X-ray frame to the anatomical roadmap to yield a registered X-ray frame, to obtain a constraint condition of the region of implantation using the anatomical roadmap, and to generate the spatial implantation envelope of the first medical device using the constraint condition.

According to an embodiment, an apparatus 82 is provided according to the previous description, wherein the first medical device is a deployable valve prosthesis, and wherein the second medical device is a pigtail catheter.

According to an embodiment, an apparatus 82 is provided as described previously, wherein the first medical device is a left atrial appendage occlusion device, and the second medical device is an electrode for use in a left atrial appendage procedure.

According to an embodiment, an apparatus 82 is provided as described previously, wherein the processing unit 84 is configured to detect the first medical device in the first X-ray frame of the plurality of X-ray frames.

Figure 8:
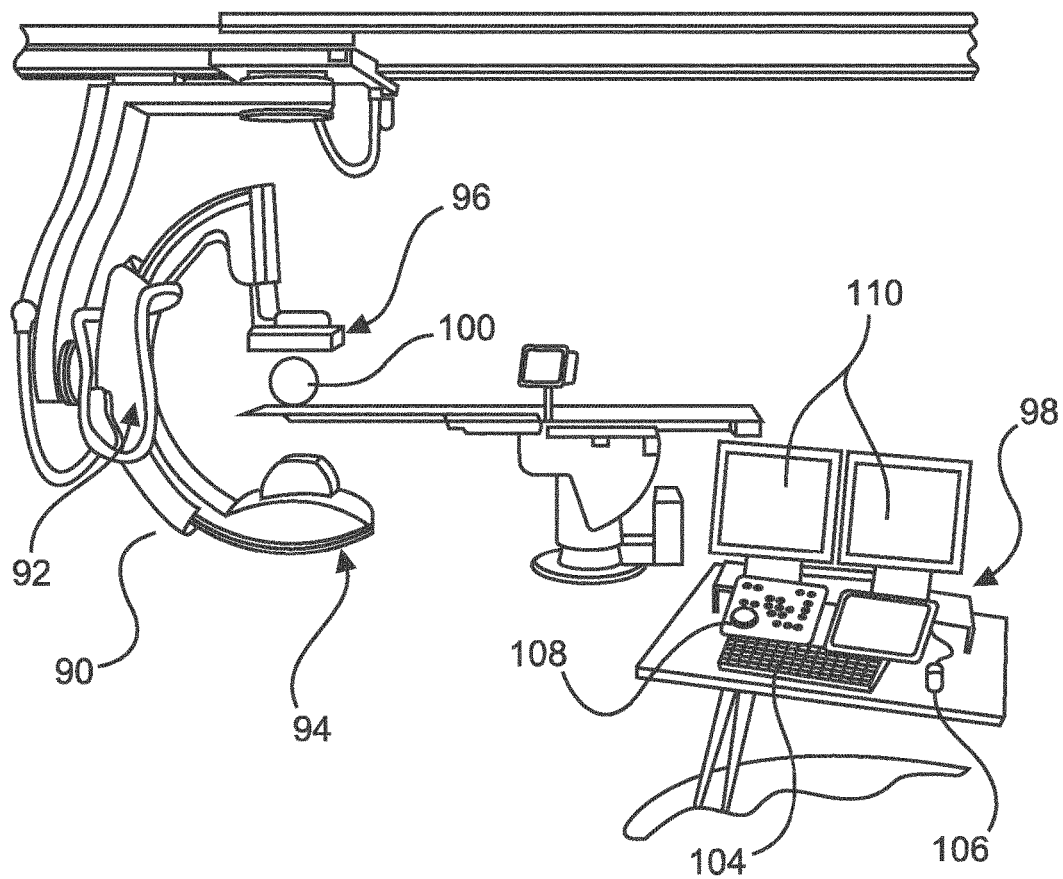
FIG. 8 shows an X-ray imaging arrangement according to a third aspect of the invention.

According to a third aspect of the invention, an X-ray imaging arrangement 90 is provided as shown in FIG. 8.

The X-ray imaging arrangement 90 comprises:

an X-ray image acquisition device 92 with an X-ray source 94 and an X-ray detector 96. The X-ray imaging arrangement also comprises an apparatus 98 for providing a medical placement alarm according to the previous description.

The X-ray image acquisition device 92 is configured to acquire image data of a region of interest 100 of a patient, and to provide the image data to an interface of the apparatus 98 for providing a medical placement alarm.

As shown in FIG. 8, the apparatus may additionally comprise a keyboard 104, a mouse 106, or a track wheel 108 for controlling the apparatus 98. Results may be provided to the user via the monitors 110. The monitor 110 may also be considered one example of an output device for providing an alarm to a medical professional.

According to a fourth aspect of the invention, a computer program element for controlling an apparatus as previously described is provided which, when the computer program element is executed by a processing unit, is adapted to perform the steps according to the previous description.

According to a fifth aspect of the invention, a computer-readable medium having stored the computer program element as previously described is provided.

A computer program element might be stored on a computer unit, which might also be a part of an embodiment of the present invention. This computing unit may be adapted to perform or induce performance of the steps of the method described above.

Moreover, it may be adapted to operate the components of the above-described apparatus. The computing unit can be adapted to operate automatically and/or to execute the orders of a user. A computer program may be loaded into a working memory of a data processor. The data processor may, thus, be equipped to carry out the method of the invention.

This exemplary embodiment of the invention covers both the computer program that has the invention installed from the beginning, and a computer program that, by means of an update, turns an existing program into a program that uses the invention.

A computer program may be stored and/or distributed on a suitable medium, such as optical storage media, or a solid state medium supplied together with, or as a part of other hardware. It may also be distributed in other forms, such as via the Internet, or other wired or wireless telecommunication systems.

However, the computer program may also be presented over a network, such as the World Wide Web, and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should be noted that embodiments of the invention are described with reference to different subject-matters. In particular, some embodiments are described with reference to method-type claims, whereas other embodiments are described with reference to the device-type claims. However, a person skilled in the art will gather from the above, and the following description that, unless otherwise notified, in addition to any combination of features belonging to one type of subject-matter, also any other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An apparatus for generating a medical device implantation warning, comprising:
   a processor; and
   an interface for receiving an X-ray image sequence comprising a plurality of X-ray frames of a region of interest of an object,
   wherein the processor is configured
      to generate a spatial implantation envelope of a first medical device to be deployed in a region of implantation, wherein the spatial implantation envelope defines a spatial extent of the region of implantation during and/or after a deployment of the first medical device, the spatial extent being around the first medical device and defined by lumen walls of a lumen into which the first medical device is being deployed, the first medical device being one of a prosthesis and an occlusion device,
      to detect, in a first X-ray frame, image data representing a second medical device located at a second medical device position inside the region of interest that coincides with spatial implantation envelope resulting in a detected intersection condition of the spatial implantation envelope and the second medical device position, wherein the second medical device is one of a catheter and an electrode, and
      in response to the detected intersection condition, to generate the medical device implantation warning.

2. The apparatus of claim 1,
   wherein the processor is further configured to detect, in the first X-ray image frame, image data representing the first medical device, having a first medical device position;
   and wherein the processor is further configured to generate the spatial implantation envelope of the first medical device at the first medical device position.

3. The apparatus of claim 1,
   wherein the processor is further configured to detect, in the first X-ray image frame, image data representing an anatomical feature,
   and wherein the processor is further configured to generate the spatial implantation envelope of the first medical device based on a recognition of the anatomical feature in said image data.

4. The apparatus according to claim 1, further comprising:
   a trigger device configured to provide a first medical device implantation trigger to the processor,
   wherein the processor is further configured, when the first medical device implantation trigger indicates that a first medical device implantation is (i) imminent, or (ii) has begun, to generate the medical device implantation warning when the detected intersection condition between the spatial implantation envelope and the second medical device position.

5. The apparatus according to claim 4,
   wherein the apparatus further comprises a warning device configured to output the medical device implantation warning.

6. The apparatus according to claim 4,
   wherein the trigger device is further configured to: provide a first medical device implantation model of the first medical device and to generate the spatial implantation envelope using the first medical device implantation model.

7. The apparatus according to claim 6,
   wherein the trigger device is configured to simulate an implantation phase between a first simulated implantation state and a second simulated implantation state of the first medical device inside the region of interest using the first medical device implantation model.

8. The apparatus according to claim 6,
   wherein the trigger device is further configured to receive a partial implantation indication;
   wherein the first medical device implantation model represents a partially deployable first medical device;
   wherein the spatial implantation envelope of the first medical device represents an intermediate implantation position of the first medical device inside the region of interest; and
   wherein the processor is configured to generate an intermediate device implantation warning upon receiving the partial implantation indication, when the intermediate implantation position intersects with the second medical device position.

9. The apparatus according to claim 8, wherein the first medical device is a deployable valve prosthesis, and wherein the second medical device is a pigtail catheter.

10. An X-ray imaging arrangement, comprising:
an XH-ray image acquisition device with an X-ray source and an X-ray detector; and
an apparatus for providing according to claim 8;
wherein the X-ray image acquisition device is configured to acquire image data of a region of interest of a patient, and to provide the image data to the interface of the apparatus.

11. A method for generating a medical device implantation warning, comprising the acts of:
providing an X-ray image sequence comprising a plurality of X-ray frames of a region of interest of an object;
generating a spatial implantation envelope of a first medical device to be deployed in a region of implantation, wherein the spatial implantation envelope defines a spatial extent of the region of implantation during and/or after a deployment of the first medical device, the spatial extent being around the first medical device and defined by lumen walls of a lumen into which the first medical device is being deployed, the first medical device being one of a prosthesis and an occlusion device,
detecting, in a first X-ray frame, image data representing a second medical device located at a second medical device position inside the region of interest that coincides with spatial implantation envelope resulting in a detected intersection condition of the spatial implantation envelope and the second medical device position wherein the second medical device is one of a catheter and an electrode; detecting an intersection condition of the spatial implantation envelope and the second medical device position; and, generating the medical device implantation warning.

12. A non-transitory computer readable medium comprising computer instructions which, when executed by a processor, configure the processor to perform a method of generating a medical device implantation warning, the method comprising the acts of:
providing an X-ray image sequence comprising a plurality of X-ray frames of a region of interest of an object;
generating a spatial implantation envelope of a first medical device to be deployed in a region of implantation, wherein the spatial implantation envelope defines a spatial extent of the region of implantation during and/or after a deployment of the first medical device, the spatial extent being around a first medical device and defined by lumen walls of a lumen into which the first medical device is being deployed, the first medical device being one of a prosthesis and an occlusion device,
detecting, in a first X-ray frame, image data representing a second medical device located at a second medical device position inside the region of interest that coincides with spatial implantation envelope resulting in a detected intersection condition of the spatial implantation envelope and the second medical device position, wherein the second medical device is one of a catheter and an electrode; and
in response to the detected intersection condition, generating the medical device implantation warning.

* * * * *